(12) United States Patent
Campin et al.

(10) Patent No.: US 12,070,270 B2
(45) Date of Patent: Aug. 27, 2024

(54) AUTOMATED ASSESSMENT OF HUMAN LENS CAPSULE STABILITY

(71) Applicant: Alcon Inc., Fribourg (CH)

(72) Inventors: John Alfred Campin, Southlake, TX (US); Martin Gründig, Rangsdorf (DE); Armin Haupt, Berlin (DE); George Hunter Pettit, Fort Worth, TX (US); Mark Andrew Zielke, Lake Forest, CA (US)

(73) Assignee: Alcon Inc., Fribourg (CH)

( * ) Notice: Subject to any disclaimer, the term of this patent is extended or adjusted under 35 U.S.C. 154(b) by 484 days.

(21) Appl. No.: 17/507,659

(22) Filed: Oct. 21, 2021

(65) Prior Publication Data

US 2022/0192485 A1 Jun. 23, 2022

Related U.S. Application Data

(60) Provisional application No. 63/129,386, filed on Dec. 22, 2020.

(51) Int. Cl.
*A61B 3/113* (2006.01)
*A61B 3/00* (2006.01)

(52) U.S. Cl.
CPC ............ *A61B 3/113* (2013.01); *A61B 3/0025* (2013.01)

(58) Field of Classification Search
CPC ..... A61B 3/113; A61B 3/0025; A61B 3/0008; A61B 3/0091; A61B 3/1173
See application file for complete search history.

(56) References Cited

U.S. PATENT DOCUMENTS

| 11,003,244 B2 * | 5/2021 | Rucci ................. G02B 27/0093 |
| 2009/0316003 A1 | 12/2009 | Hirsa et al. |
| 2020/0064914 A1 | 2/2020 | Rucci et al. |

FOREIGN PATENT DOCUMENTS

| EP | 3046459 B1 | 8/2019 |
| JP | 2003164425 A | 6/2003 |
| WO | 2015109145 A1 | 7/2015 |

OTHER PUBLICATIONS

Darius Vitonis, et al., Person Identification using Eye Movements and Post Saccadic Oscillations, 2014 Tenth International Conference on Signal-Image Technology & Internet-Based Systems, Nov. 23, 2014, pp. 580-583.

(Continued)

*Primary Examiner* — James C. Jones

(57) ABSTRACT

A method for assessing a lens capsule stability condition in an eye of a human patient includes directing electromagnetic energy in a predetermined spectrum onto a pupil of the eye, via an energy source, concurrently subsequent to a movement of the eye causing eye saccades to occur therein. The method also includes acquiring images of the eye indicative of the eye saccades using an image capture device, and computing, via the ECU, a motion curve of the lens capsule using the images. Additionally, the method includes extracting time-normalized lens capsule oscillation traces based on the motion curve via the ECU, and then model-fitting the lens capsule oscillation traces via the ECU to thereby assess the lens capsule instability condition. An automated system for performing an embodiment of the method is also disclosed herein, including the energy source, image capture device, and ECU.

20 Claims, 3 Drawing Sheets

(56) References Cited

OTHER PUBLICATIONS

Tabernero, et al., Lens Oscillations in the Human Eye. Implications for Post-Saccadic Suppression of Vision, Plos One, Apr. 22, 2014, pp. 1-6, Volume/Issue 9/4.

* cited by examiner

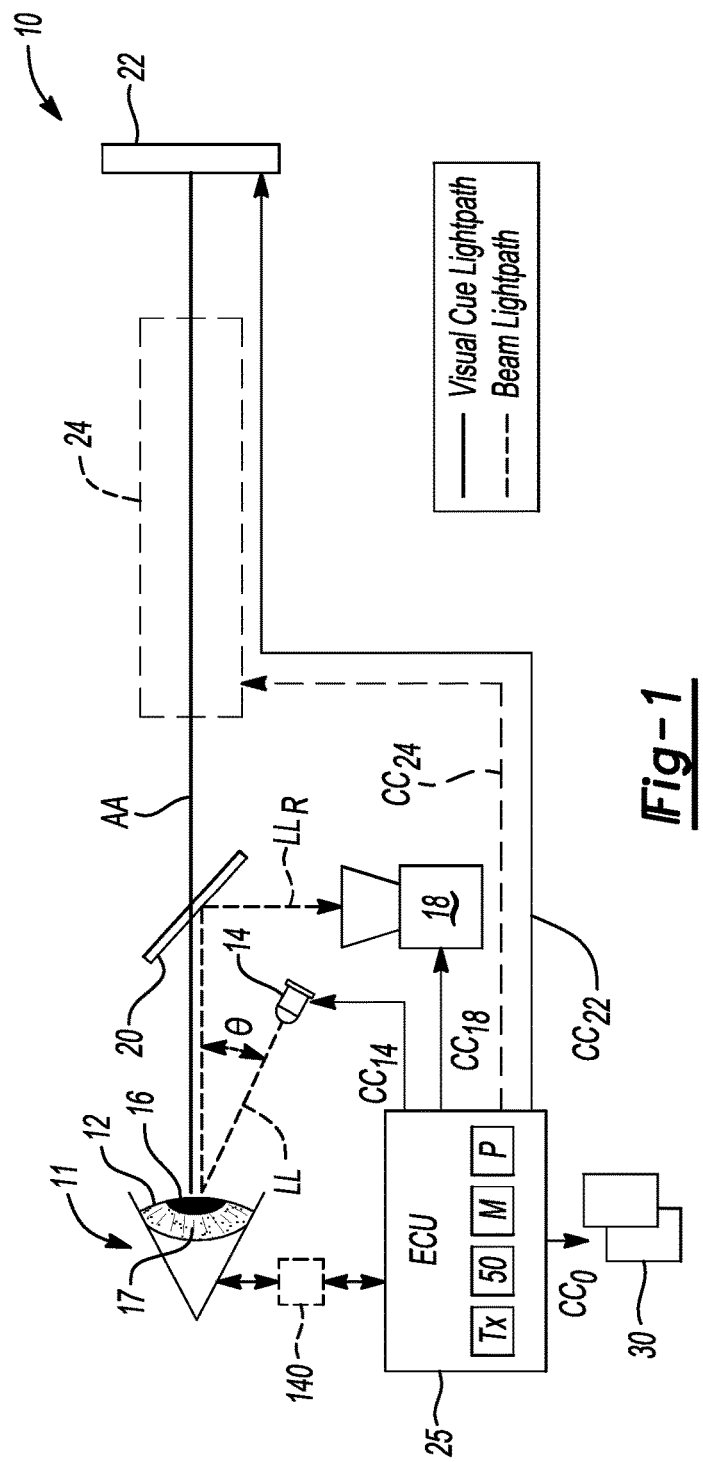
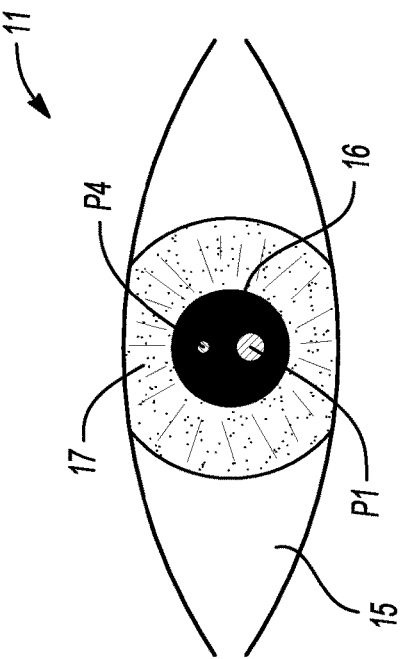
Fig-1
Fig-2

AUTOMATED ASSESSMENT OF HUMAN LENS CAPSULE STABILITY

INTRODUCTION

The present disclosure relates to automated methods and systems for non-invasively diagnosing or assessing latent lens capsule stability within an eye of a human patient. A non-limiting example lens stability condition that may be effectively diagnosed in accordance with the present teachings is that of zonular insufficiency (ZI). Additionally, the solutions described herein may be tailored to assessing a candidate patient for an accommodative intraocular lens (aIOL) device, e.g., during a pre-operative fitting process, when determining an optimal cataract surgical plan, or when assessing the patient's accommodation potential. Similarly, other pre-operative, pos-operative, diagnostic, or treatment procedures related to lens capsule stability or general ocular health may benefit from the present teachings.

The lens of a human eye includes the lens capsule, epithelium, and supporting fibers. The lens capsule in particular is a thin, transparent membrane, the outer periphery of which is securely attached to a ring of elastic fibers referred to in the art as Zinn's membrane/zonules of Zinn, or simply as zonules. Ciliary muscles within the eye contract or relax to collectively act on the zonules during accommodation, which has the effect of changing the shape of the lens capsule. Zonules therefore benefit proper ocular function by securing the lens capsule along the optical axis while properly accommodating the various forces imparted to the lens by the ciliary muscles.

The above-noted ZI condition is present when the zonules are excessively resilient or "floppy". Consequently, the lens and the capsular bag may become less securely attached to the ciliary muscles. As a result, a patient diagnosed with a ZI condition may be at an increased risk for certain complications during cataract surgery, lens replacement, or aIOL device implantation. A surgeon operating on a ZI patient might attempt to mitigate surgical risk by employing a capsular support device to stabilize the capsular bag, by performing a laser-based capsularhexis procedure, or by taking other precautionary measures.

Zonule size is on the order of tens of micrometers. The miniscule size and the well-shielded location of the zonules behind the iris precludes an effective direct optical examination of zonular structural integrity. The presence of a ZI condition in a given patient is therefore typically revealed indirectly, e.g., using a slit lamp exam during which the surgeon imparts a stimulus to the patient's body to induce eye movement. For instance, a clinician may tap a headrest supporting the patient's head to impart a manual stimulus, or may gently tap the side of the patient's head directly. An ultrasonic stimulus may be used in an alternative approach.

Using either approach may lead to an increase in patient anxiety as the patient anticipates arrival of the stimulus. The ultrasonic stimulus in particular generally requires direct contact of an ultrasonic measurement device with the patient's eye. Moreover, the diagnostic result tends to be highly skill-dependent and subjective. As a result, a latent ZI condition or other lens capsule instability conditions may be unexpectedly discovered, e.g., during eye surgery, which could adversely affect surgical results or require changes to the surgical plan.

SUMMARY

Disclosed herein are methods and systems for performing automated assessments of the structural integrity of a lens capsule of the human eye. The present teachings may be used for detecting latent lens capsule instability conditions that may be predictive of potential lens or lens capsule dislocation. By way of example and not of limitation, the present teachings may be applied to evaluating zonular conditions and/or patient potential for an accommodative intraocular lens or another surgical procedure. The present approach includes measuring and quantifying lens oscillations in the course of accurately and repeatably diagnosing such conditions.

An embodiment of the method for assessing a lens capsule instability condition includes directing electromagnetic energy in a predetermined spectrum onto a pupil of the eye, via an energy source, concurrently subsequent to a movement of the eye causing eye saccades to occur therein. The method includes acquiring images of the eye indicative of the eye saccades using an image capture device, and thereafter computing, via an electronic control unit (ECU), a motion curve of the lens capsule using the images. The method further includes extracting time-normalized lens capsule oscillation traces based on the curve via the ECU, and then model-fitting the lens capsule oscillation traces via the ECU to thereby assess the lens capsule instability condition.

Optional implementations of the method may include transmitting a dynamic gaze-guiding cue to a visual target, with the visual target being arranged along the patient's line-of-sight. The gaze-guiding cue induces predetermined and controlled eye movements, referred to hereinbelow and in the general art as eye saccades, with the induced eye saccades occurring concurrently with the inducement of the characteristic Purkinje reflexes in the light-based embodiments.

As part of such light-based embodiment of the present method, one or more images of characteristic Purkinje reflexes may be collected using a high-speed camera, with an electronic control unit (ECU) computing a motion curve for one of the characteristic Purkinje reflexes, e.g., the P1 reflex as described herein. Other embodiments may forego the inducing and detection of Purkinje reflexes in favor of capturing other reflexes or motions indicative of lens capsule oscillations when diagnosing lens/capsule structural integrity as set forth herein.

The method also includes extracting time-normalized lens oscillation traces based on the motion curve(s) via the ECU, and thereafter model-fitting the time-normalized lens oscillation traces to diagnose the above-noted lens/capsule structural condition.

A system for diagnosing a lens/capsule condition is also disclosed herein. According to a representative embodiment, the system includes an energy source, e.g., IR or visible light, ultrasonic energy, etc. The energy source is operable for directing electromagnetic energy toward a target location, with the target location coinciding with the location of an eye of the human patient during operation of the system. The system includes an image capture device. When the image capture device is a high-speed camera, a hot mirror may be arranged at a predetermined angle with respect to the camera. Such a mirror may be configured to direct reflected light from the target location toward the camera. The optional gaze-guiding visual target may be positioned opposite the target location. The ECU when used as part of such a system is in communication with the energy source, the image capture device, and the optional gaze-guiding visual target.

In a representative embodiment in which the electromagnetic energy includes light waves in the visible or IR spectrum, such light may be directed onto the pupil at predetermined intensity level sufficient for inducing characteristic Purkinje reflexes in the patient's pupil. The ECU may be configured to transmit a gaze-guiding cue to the visual target in some embodiments, which may occur concurrently with inducing the characteristic Purkinje reflexes to thereby cause the visual target to change relative position. The change of relative position in this instance is one that is sufficient for inducing saccades in the eye. As noted above, however, other types of imaging may be used in other embodiments, and therefore characteristic Purkinje reflexes are just one possible reflex within the scope of the present disclosure.

The ECU is also configured to acquire images of the characteristic Purkinje or other ocular reflexes, e.g. using the high-speed camera or an ultrasonic readout, and to thereafter compute one or more motion curves of a predetermined one of the characteristic ocular reflexes using a processor. The ECU extracts time-normalized lens oscillation traces based on the curves, and is also configured to perform model-fitting of the time-normalized lens oscillation traces via the processor using a predetermined lumped mass model. The ECU or a practitioner/surgeon using the ECU then diagnoses the potentially unstable lens/capsule condition using the results of such model-fitting.

The ECU in another possible embodiment is configured for use with a high-speed video camera. The ECU in this embodiment includes a processor, a transceiver in communication with the high-speed video camera and a visual target, and memory on which is recorded computer-readable instructions. Execution of the instructions by the processor causes the processor to receive images of a P1 characteristic Purkinje reflex from the high-speed camera when an IR light beam is directed onto a pupil of the eye.

Likewise, execution of the instructions causes the ECU to transmit a dynamic gaze-guiding cue to the visual target to thereby move the visual target sufficiently for inducing predetermined eye saccades, which occurs concurrently with the characteristic Purkinje reflexes. The ECU in this particular embodiment computes an instantaneous velocity, acceleration, and/or position curve of the P1 characteristic Purkinje reflex, extracts time-normalized lens oscillation traces based on the motion curve(s), and model-fits the lens oscillation traces using a lumped mass model to thereby diagnose the zonular condition.

The above-described features and advantages and other possible features and advantages of the present disclosure will be apparent from the following detailed description of the best modes for carrying out the disclosure when taken in connection with the accompanying drawings.

BRIEF DESCRIPTION OF THE DRAWINGS

FIG. 1 is a schematic illustration of an automated system for diagnosing or assessing latent lens/capsule-related structural conditions in accordance with the present disclosure.

FIG. 2 is a schematic depiction of a typical characteristic Purkinje reflexes within a pupil of a human eye.

Figure 3:
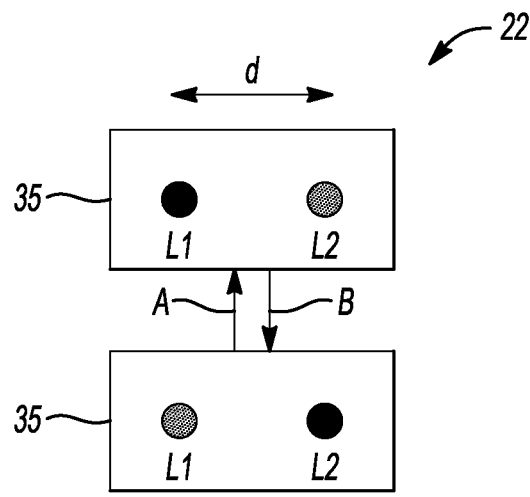
FIG. 3 is a schematic illustration of exemplary sequence of alternating or dynamic visual cues usable as an optional part of the present method.

The foregoing and other features of the present disclosure will become more fully apparent from the following description and appended claims, taken in conjunction with the accompanying drawings. Understanding that these drawings depict only several embodiments in accordance with the disclosure and are not to be considered limiting of its scope, the disclosure will be described with additional specificity and detail through the use of the accompanying drawings. Any dimensions disclosed in the drawings or elsewhere herein are for the purpose of illustration only.

DETAILED DESCRIPTION

Embodiments of the present disclosure are described herein. It is to be understood, however, that the disclosed embodiments are merely examples and other embodiments can take various and alternative forms. The figures are not necessarily to scale; some features could be exaggerated or minimized to show details of particular components. Therefore, specific structural and functional details disclosed herein are not to be interpreted as limiting, but merely as a representative basis for teaching one skilled in the art to variously employ the present disclosure. As those of ordinary skill in the art will understand, various features illustrated and described with reference to any one of the figures can be combined with features illustrated in one or more other figures to produce embodiments that are not explicitly illustrated or described. The combinations of features illustrated provide representative embodiments for typical applications. Various combinations and modifications of the features consistent with the teachings of this disclosure, however, could be desired for particular applications or implementations.

Certain terminology may be used in the following description for the purpose of reference only, and thus are not intended to be limiting. For example, terms such as "above" and "below" refer to directions in the drawings to which reference is made. Terms such as "front," "back," "fore," "aft," "left," "right," "rear," and "side" describe the orientation and/or location of portions of the components or elements within a consistent but arbitrary frame of reference which is made clear by reference to the text and the associated drawings describing the components or elements under discussion. Moreover, terms such as "first," "second," "third," and so on may be used to describe separate components. Such terminology may include the words specifically mentioned above, derivatives thereof, and words of similar import.

Referring to the drawings, wherein like reference numbers refer to like components, an automated assessment system 10 is depicted schematically in FIG. 1. The system 10 is configured for inferring structural integrity of lens/capsule structure within an eye 11 of a human patient, such as but not limited to the structural integrity of zonules and/or other tissue located behind a cornea 12 and iris 17 of the eye 11. For example, such a diagnosis or assessment may be of a zonular insufficiency (ZI) condition or other conditions related to lens/capsulate stability as noted herein, with the diagnosed condition represented by metrics generated through the integrated processes of video tracking, image analysis, and physical modeling.

Use of the present teachings in conjunction with preoperative and post-operative ocular assessments may help improve the results of cataract surgical planning, e.g., by more accurately identifying potential intraoperative risks and aiding in optimal lens selection. Used postoperatively with pseudophakic eyes, the present teachings may also help diagnose visual impairment linked to various zonular problems. Likewise, the present teachings may be beneficial to a host of other optical or ophthalmological procedures and/or diagnostics, as will be appreciated by those skilled in the art.

As set forth herein with particular reference to FIGS. 2-5C, the automated assessment system 10 of FIG. 1 may be used to infer lens/capsule stability by measuring movements of a crystalline lens located within the eye 11 during rapid eye movements or saccades. The system 10 automatically tracks infrared light reflected from the cornea 12 and lens in some embodiments. Due to the elastic suspension of the lens on zonular fibers, lens movement relative to the remaining eye tissue starts with a slight delay and finishes with an overshoot with characteristic oscillations. ZI and other ocular conditions are broadly characterized by pronounced lens instability, which itself results in altered lens/capsule oscillations. Model-based quantification of such altered oscillations is thus used as part of the present method 50. As a result, the approach set forth herein can be used to diagnose certain conditions of the eye 11 in a more accurate and patient-friendly manner relative to slit lamps and other competing approaches.

A possible non-limiting embodiment of the automated assessment system 10 shown in FIG. 1 includes an energy source 14 operable for directing electromagnetic energy (arrow LL), e.g., light or ultrasonic energy, onto a pupil 16 of the eye 11. In a possible application, the energy source 14 is an infrared (IR) light source, and the electromagnetic energy (arrow LL) is in the form of an IR light beam in an eye-safe portion of the IR spectrum. During operation of the system 10, the pupil 16 thus forms a target location for irradiation by the electromagnetic energy (arrow LL). In addition to the light source 14, the system 10 may include an image capture device 18 such as a high-speed camera. When the image capture device 18 is so embodied, the system 10 may also include a hot mirror 20, with the latter being arranged at a predetermined angle ($\theta$) with respect to an optical axis (AA), with $\theta$ being about 15° in a possible implementation. The hot mirror 20 is thus configured to direct reflected energy (arrow $LL_R$) from the pupil 16 toward the image capture device 18. Alternatively, an ultrasonic transducer 140 may be used to directly image the lens capsule within the eye 11 in lieu of light-based motion detection and tracking.

As part of the automated assessment system 10, an optional gaze-guiding visual target 22 is positioned along the optical axis (AA) opposite the patient. An electronic control unit (ECU) 25 as described in further detail below is in communication with the energy source 14, the image capture 18, and the optional gaze-guiding visual target 22, with the ECU 25 being configured to execute computer-readable code or instructions embodying the present method 50. Although shown schematically as a unitary box schematic for illustrative simplicity, the ECU 25 may include one or more networked devices, computer-readable media or memory (M), including a non-transitory (e.g., tangible) medium that participates in providing data/instructions that may be read by one or more processors P.

The memory (M) may take many forms, including but not limited to non-volatile media and volatile media. As will be appreciated, non-volatile media may include, for example, optical or magnetic disks and other persistent memory, while volatile media may include dynamic random-access memory (DRAM), static RAM (SRAM), etc., any or all of which may constitute a main memory. Other hardware not depicted but well established in the art may be included as part of the ECU 25, including but not limited to input/output circuitry, a local oscillator or high-speed clock, buffers, latches, etc.

With respect to the various constituent components of the automated assessment system 10 depicted in FIG. 1, the energy source 14 may be optionally embodied as an application-suitable source of IR light having a wavelength falling within an eye-safe portion of the electromagnetic spectrum, for instance IR wavelengths greater than about 1.4 µm. Suitable options for use as the energy source 14 in such a non-limiting example embodiment may include IR light-emitting diodes (LED), continuous wave lasers, etc. Although omitted for illustrative simplicity and clarity, the energy source 14 may be coupled to and/or inclusive of a power supply, filters, amplifiers, waveguides, and other components suitable for ensuring generation and propagation of the electromagnetic energy (arrow LL) of application-suitable quality.

The hot mirror 20 may be embodied as a heat-reflecting mirror operating as a short-pass edge filter, i.e., configured to transmit visible wavelengths of incident light while reflecting IR/heat-generating wavelengths toward the image capture device 18. The ECU 25 in this particular embodiment is configured, during operation of the system 10, to control operation of the energy source 14 so as to direct the electromagnetic energy (arrow LL) onto the pupil 16 of the eye 11. In some embodiments, corrective optics 24 may be arranged along the optical axis (AA) between the eye 11 and the visual target 22 to ensure proper fixation and tracking of the patient's focus on the moving gaze cue. Such corrective optics 24 may be used to advantage with myopic patients or patients having other visual impairments, such as spherical/cylindrical defects, as an optional module for corrective optics. Although omitted from FIG. 1 for clarity and simplicity, the corrective optics 24 may include mounts for manually-switchable lenses, liquid lenses, and/or a fogging system in various embodiments.

As part of the present approach, the electromagnetic energy (arrow LL) arrives at a predetermined intensity level that is sufficient for inducing characteristic reflexes in the pupil 16, e.g., Purkinje reflexes. The electromagnetic energy (arrow LL) is directed onto the pupil 16, where the incident electromagnetic energy (arrow LL) propagates through and is reflected by the cornea 12 and lens (not shown). Irradiation in this manner will, in an IR/light-based embodiment, give rise to four characteristic Purkinje reflexes, with the first and fourth characteristic Purkinje reflexes P1 and P4 shown in FIG. 2 and used herein in some embodiments.

Referring briefly to FIG. 2, a schematic illustration of the eye 11 includes the iris 17 centered within the surrounding sclera 15, i.e., the whites of the eye 11. The Purkinje reflexes, also referred to in the art as Purkinje images or Purkinje-Samson images, manifest as the externally-visible reflection of an object within the pupil 16. The P1 Purkinje reflex, which tends to be the brightest of the Purkinje reflexes, is visible on the outer area of the cornea 12 (see FIG. 1) within the area of the pupil 16. The P4 Purkinje reflex, which is inverted, is visible on the posterior surface of the cornea 12 likewise within the area of the pupil 16. The P2 and P3 Purkinje reflexes, both of which are omitted from FIG. 2, are visible on the inside and anterior surface of the cornea 12. Thus, during operation of the system 10 of FIG. 1, reflected light from the eye 11 is purposefully deflected by the angled hot-mirror 20 in the direction of the image capture device 18, which in turn runs at an application-suitable high frequency, e.g., a shutter speed of greater than about 300 Hz. Different technologies, for example optical coherence tomography (OCT) or ultrasonic biomicroscopy (UBM) might be used for lens position tracking in other embodiments, possibly with directly imaged features of the lens/capsule structure in lieu of the above-described Purkinje reflexes.

Referring again to FIG. 1, as part of the present method 50 described below with particular reference to FIG. 4, the ECU 25 may be optionally configured to transmit a gaze-guiding cue signal (arrow $CC_{22}$) to the visual target 22 concurrently with inducing lens/capsule motion. The optional gaze-guiding cue signal (arrow $CC_{22}$) causes the visual target 22 to change its relative position to a level sufficient for inducing predetermined saccades of the eye 11, and as a result, for inducing detectable oscillations of the lens/capsule located therewithin.

As shown in FIG. 3, for example, transmitting the gaze-guiding cue signal (arrow $CC_{22}$) to the visual target 22 may include separately illuminating respective lighting devices L1 and L2 of a lighting panel 35. The lights L1 and L2 may be optionally embodied as two (or more) discrete LEDs, incandescent bulbs, or other rapidly illuminating light sources spaced apart from each other by a distance (d) and sequentially illuminated according to a predetermined sequence. The gaze-guiding cue signal (arrow $CC_{22}$) could be implemented as a pair of side-by-side LEDs, for example, that are switched on and off in an alternating manner as indicated by arrows A and B, e.g., by action of the ECU 25 or another control device. Other embodiments may be envisioned, such as but not limited to projection or display of a dynamic object at alternating positions, e.g., a video display configured to depict a dynamic image, or any other suitable configuration. When the patient tracks the moving target, the eye 11 is caused to move through a predetermined range of motion, with such eye movements inducing lens oscillations in a controlled and repeatable manner.

The ECU 25 of FIG. 1 is also configured to acquire a set of images of the eye 11. This may include directly imaging the lens/capsule as noted above, or it may involve indirect imaging by capturing the characteristic Purkinje reflexes P1 and P2 via transmission of capture control signals (arrow $CC_{18}$) to the image capture device 18, as noted above, in conjunction with transmission of energy control signals (arrow $CC_{14}$) to the energy source 14. The ECU 25 thereafter computes a motion curve of the imaged lens/capsule motion via the processor(s) (P) that is descriptive of motion of the lens capsule. This may entail computing instantaneous velocity, acceleration, position, and/or other curves of a predetermined one of the characteristic Purkinje reflexes, such as the first characteristic reflex P1, or of any directly-imaged landmark structure of the eye 11, e.g., the lens itself. Additionally, the ECU 25 is configured to extract time-normalized lens oscillation traces based on the motion curve(s), and to thereafter perform model-fitting of the lens oscillation trace via the processor (P) using a lumped mass model. The latent lens/capsule condition is then diagnosed using results of such model-fitting, with the ECU 25 possibly outputting a data file 30 as part of an output signal (arrow $CC_O$).

Figure 4:
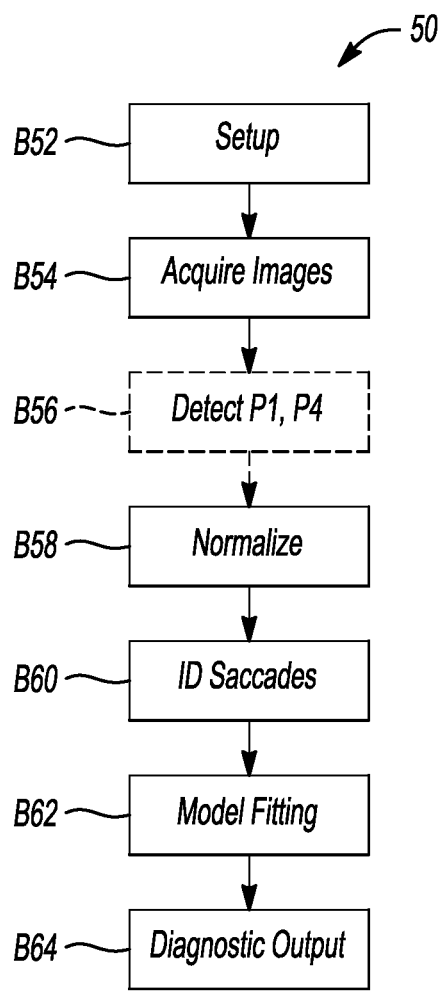
FIG. 4 is a flow chart describing an exemplary method for diagnosing lens/capsule conditions of the types set forth herein.

Referring to FIG. 4, the method 50 for inferring/diagnosing a latent lens/capsule structural instability condition within the eye 11 (FIGS. 1 and 2) of a human patient commences with block B52 ("Setup"), which may entail arranging a human patient with respect to the automated assessment system 10 of FIG. 1. For instance, the patient may be comfortably seated in a chair facing in a particular direction, such as toward the optional visual target 22, with the image capture device 18 located adjacent to the hot-mirror 20 and the energy source 14 in some embodiments. The patient then directs her gaze toward the visual target 22 and maintains this posture as the method 50 proceeds to block B54.

At block B54, the practitioner controlling the automated assessment system 10 or the ECU 25 itself initiates operation of energy source 14 via the energy control signals (arrow $CC_{14}$) to direct the electromagnetic energy (arrow LL of FIG. 1) toward the eye 11 while the patient maintains focus on the visual target 22. In a light-based implementation in which the lens/capsule is indirectly imaged, the electromagnetic energy (arrow LL) is maintained at an intensity level that is sufficient for inducing characteristic Purkinje reflexes P1 and P4 within the pupil 16. If the optional corrective optics 24 are employed as part of block B52, then block B54 may entail viewing the visual target 22 through the intervening corrective optics 24 to aid the patient in focusing on the visual target 22 in a manner that is based on the patient's visual acuity. Transmitting the optional dynamic gaze-guiding cue (arrow $CC_{22}$) to the visual target 22 arranged along a line-of-sight of the eye 11 to thereby induce eye saccades concurrently with the characteristic Purkinje reflexes. Such a dynamic gaze-guiding cue (arrow $CC_{22}$) may also be used if desired in embodiments in which the lens/capsule is directly imaged as opposed to imaging the Purkinje reflexes.

As this is ongoing, the ECU 25 may acquire video, still, ultrasonic, or other images of the eye 11, possibly inclusive of the characteristic Purkinje reflexes, using the image capture device 18. That is, as the patient's optical axis changes in conjunction with a moving image on the visual target 22, the image capture device 18 continuously acquires images and saves the collected images to memory (M) of the ECU 25. Alternatively, the ECU 25 may save discrete image sequences for each saccade defined by a time interval before and after the occurrence of each optional gaze-guiding visual cue (arrow $CC_{22}$). The latter approach may help minimize data transfer load and subsequent image processing time. The method 50 may then continue to optional block B56.

Block B56 may be used in embodiments using IR or other light to induce Purkinje reflexes. In such a case, block B56 entails detecting and identifying the first and fourth characteristic Purkinje reflexes P1 and P4 (see FIG. 2) within the patient's eye 11 based on predetermined factors, e.g., intensity, size, shape, absolute position, and/or relative position, i.e., of reflex P1 with respect to reflex P4 or vice versa. As part of block B56, the processor(s) (P) of the ECU 25 may extract corresponding coordinates of the reflexes P1 and P4 based on a geometrical feature of each, for example the centroid, as will be appreciated by those of ordinary skill in the art. The method 50 then proceeds to block B58.

At block B58 of the method 50 depicted in FIG. 4, the ECU 25 may normalize the data from block B56, or from an analogous block in which the lens/capsule is directly imaged. For example, the ECU 25 may extract lens movements and then correct for rotation of the eye 11. In implementations capturing P1 and P4 Purkinje reflexes, for instance, this may entail subtracting the coordinates of the first reflex P1 from the P4 coordinates. As part of block B58, the ECU 25 may identify saccade identification to extract time-normalized lens oscillation traces. Individual saccades of the eye 11 may be identified, for instance, by computing motion curves of a point of interest e.g., of reflex P1. Detected velocity spikes representing the presence of saccades, with lens oscillations occurring after such a velocity spike re-approaches zero. The method 50 then proceeds to block B60.

Block B60 of this particular embodiment of the method 50 includes performing model-fitting on the collected oscillation traces via the ECU 25 to thereby diagnose a latent lens/capsule structural instability condition. Two non-limiting example diagnostic applications for lens oscillation measurements in accordance with the present disclosure include the detection of Zonular Insufficiency (ZI) and the detection of accommodative IOL (aIOL) fitting, as noted generally above, along with a host of other lens stability-related conditions of the eye 11.

For ZI detection in particular, measuring fiber integrity of the zonules within the eye 11 may be performed by estimating zonular tension based on the collected lens oscillation data. A possible algorithmic approach uses a dynamics model to fit the collected data, i.e., to estimate the lens mass based on OCT biometry or other methodologies, and then fits the model to oscillation frequency and amplitude based on saccadic eye stimulus, e.g., least squares fit by adjusting stiffness and damping terms. The ECU 25 could for instance solve for a stiffness parameter k, which correlates to zonular tension. A simple linear lumped mass model may be sufficient for this application, while more complex models may be used to improve the fit to a given set of data.

For aIOL fitting applications of the present teachings, the approach to measure accommodative function may include estimating zonular tension during different accommodative states, and thereafter inferring ciliary muscle activity based on the lens oscillation data. In a possible algorithmic approach, the ECU 25 of FIG. 1 could use a dynamic model to fit to the data, and to estimate lens mass based on OCT biometry or other methods suitable for fitting the model to oscillation frequency and amplitude. Such an approach is likewise based on saccadic eye stimulus at different accommodative states, e.g., using a least squares fit by adjusting the stiffness and damping terms to solve for stiffness parameter k, and accommodative motion/tension range $x_0$. A nonlinear lumped mass model may be used for this purpose.

Figure 5A:
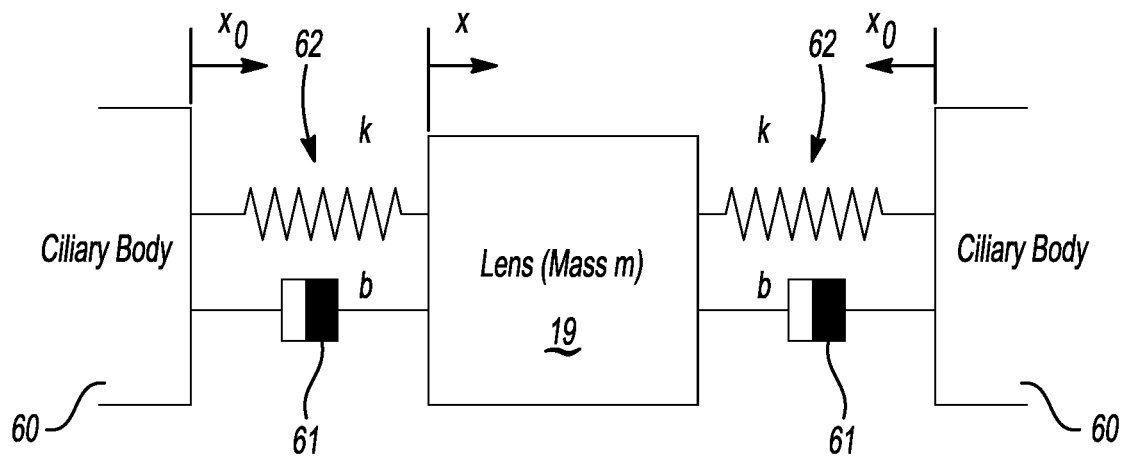
FIGS. 5A, 5B, and 5C are schematic block diagrams of representative lumped mass models of saccadic lens oscillations usable within the scope of the disclosure.
Figure 5B:
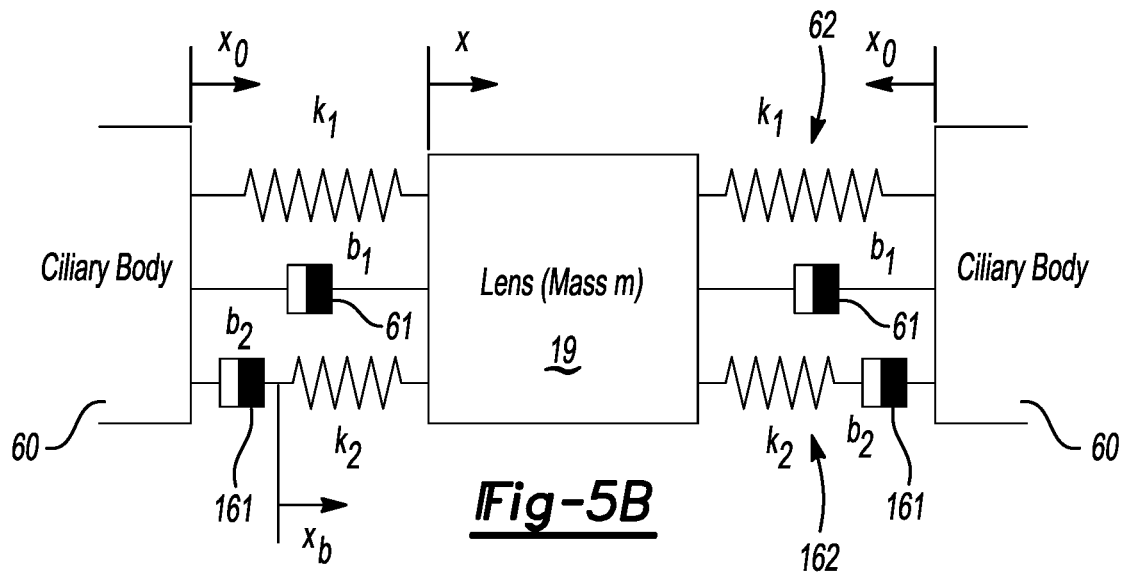
Figure 5C:
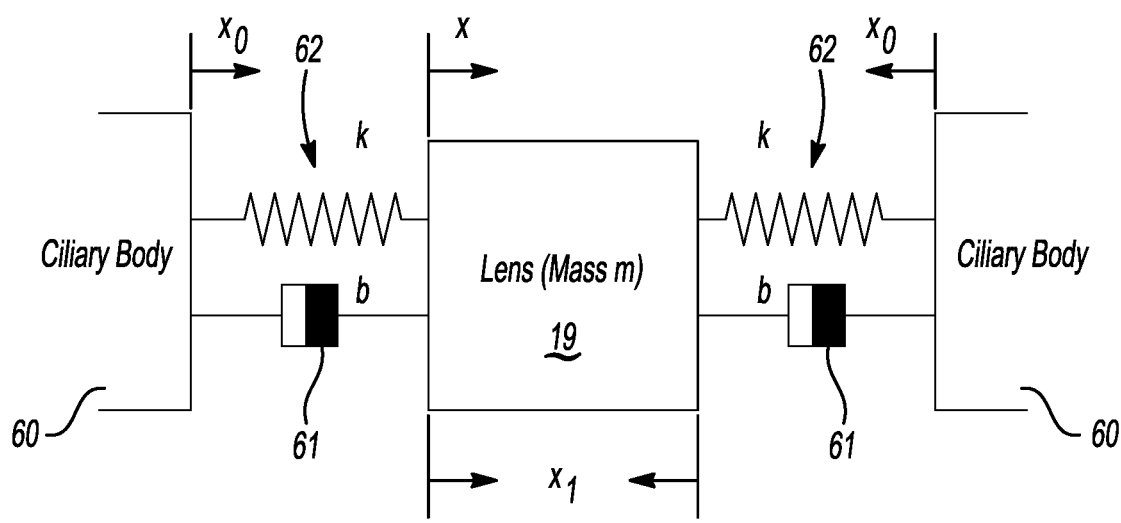

Further with respect to block B60, example lumped mass dynamic models usable within the context of the method 50 are depicted in FIGS. 5A, 5B, and 5C. A one-dimensional lumped mass model is able to describe system-level behavior for saccadic eye motion. As shown in FIG. 5A, a simplified representation of the radial arrangement of zonular fibers connect a lens 19 having a mass m to a ciliary muscle/ciliary body 60 such that the lens 19 is suspended from two anchoring points, i.e., the ciliary body 60, by two springs 62 having a spring constant k. The springs 62 in FIG. 5A represent the zonular fibers. Pretension is representative of ciliary muscle contraction status, and is given by $x_0$, i.e., the distances of the anchoring points from the mass (m). Damping influence of the physiological environment is represented by dashpots 61 in a parallel arrangement with the springs 62, with the dashpots 61 having a damping coefficient b.

With respect to $x_0$, this value is a potential suitability indicator for aIOLs. Decreasing tension during increasing accommodative demands indicates the presence of contraction of the ciliary body 60, while a lack of a tension change indicates a lack of such contraction. With respect to the spring constant k, this value correlates to stiffness of the system, primarily the zonular tension. The lack of stiffness may thus indicate potential surgical challenges.

For a linear oscillator, the system in question can be described mathematically as follows:

$$m\ddot{x}+b\dot{x}+kx=F(t) \qquad \text{Equation (1)}$$

where m once again is the lumped mass of the lens 19 and x is the linear displacement of the lens 19 in a resonant mode. The value $b\dot{x}$ is the damping term, kx is the restoring force, and F(t) is the saccadic actuation force based on the saccadic acceleration profile.

For a more complex non-linear oscillator, the response amplitude changes for different accommodative statuses, i.e., ciliary movement represented by $x_0$, indicating non-linearity. Such non-linearity is likely part of the restoring and damping forces. Thus, Equation (1) may be modified as follows:

$$m\ddot{x}+b(\dot{x},x)+kx=F(t) \qquad \text{Equation (2)}$$

In a non-linear oscillator, the damping term $b(\dot{x})$ of Equation (1) becomes the non-linear function $b(\dot{x}, x)$ of Equation (2), which can be a very complex nonlinear term inclusive of terms such as squeeze film damping or a combination of viscoelastic properties. For instance, the nonlinear function $b(\dot{x}, x)$ of Equation (2) may be represented as follows:

$$b(\dot{x},x)=b\cdot\text{sgn}(\dot{x})|\dot{x}^m|\cdot|\dot{x}^n|, \text{ or}$$

$$b(\dot{x},x)=b\cdot\text{sgn}(\dot{x})|\dot{x}^n|\cdot|(x+x_0)^p+(x-x_0)^p|$$

Non-linear behavior of the restoring force k(x) can be described as a nonlinear spring with a nonlinear spring force, e.g.:

$$k(x)=k_{\textit{eff}}(x+x_0)^p+k_{\textit{eff}}(x-x_0)^p.$$

An example non-linear model is depicted schematically in FIG. 5B. The modified lumped mass model incorporates a viscoelastic model of damping, represented by a Maxwell damping term. The Maxwell damping term assumes another dashpot 161 in series with another spring 162, and represents material properties such as creep and elasticity, properties of zonules that are well established in the art.

If natural lens shape is measured during accommodation, for example using OCT, the effects of a presbyopic lens 19 may be considered in the non-linear model of FIG. 4C by introducing another parameter xi, referred to herein as the additional lens shape parameter.

Referring again to FIG. 4, at block B62 the method 50 includes computing a metric, e.g., by including different coefficients of the mechanical model or models as set forth above. Alternatively, separate metrics could be computed based on key coefficients indicative of, e.g., surgical issues, suitability for accommodative IOL selection, recommendations, etc. Different values of the single or multiple metrics will drive recommendations for a host of beneficial processes, such as planning surgery according to indicated surgical issues, or determining suitability of a given patient to receive an accommodative IOL. The boundaries of the metric for these particular recommendations may be defined with patient cohorts in clinical studies.

Another potential implementation of the present technology could be to determine the suitability of presbyopic patients for receiving ciliary muscle-driven accommodative IOLs by measuring their residual accommodation. For example, see U.S. Pat. No. 9,456,739B2 to Campin et al. issued on Oct. 4, 2016, which is hereby incorporated by reference in its entirety. aIOLs are designed to retain the ability to accommodate after transplantation, and to this end rely on the proper functioning of the ciliary muscle. In a healthy eye, the ciliary muscle is relaxed during fixation to a far object. This in turn places the zonular fibers and capsular bag under tension, with such tensions ultimately transmitted to the lens. The lens is consequently flattened.

During accommodation of the eye 11 of FIGS. 1 and 2 to nearer objects, therefore, the ciliary muscle contracts, thereby reducing tension on zonular fibers and the capsular bag. The reduced tension allows the lens to increase its optical power. This difference in tension of zonular fibers induces different lens wobble behaviors, with accommodative states inducing stronger lens wobble than non-accommodative or far-focusing states. This effect is pronounced in presbyopic eyes. The proposed mechanical models used as part of present method 50 can therefore be used to derive zonular tension from lens wobble measurements. Comparing the tension values from the disclosed measurements over a range of accommodative demands allows for quantitative inference of ciliary muscle activity. That is, when the ciliary muscle contracts, the tension decreases with increasing accommodative demands. When no tension change is detected, the diagnostic result that may be captured in the output file 30 of FIG. 1 is that ciliary muscle activity is negligible.

Proper ciliary muscle activity response is critical for the function of many new accommodative IOL designs, and may be an important screening factor prior to cataract surgery. When used for diagnosing residual accommodative potential, the example hardware setup of FIG. 1 requires the presence of optics that can present different accommodative demands to the subject. This could be achieved, as noted above, by introducing the corrective optics 24 of FIG. 1 into the optical path in a manner that can be easily exchanged or tuned. Measurements in this instance are carried out with the visual target 22 perceived at two or more different accommodative demands. The data analysis pipeline may be similar for image analysis. The most significant difference when applying the present teachings to accommodative assessments is the higher complexity of the underlying mechanical models used as part of the method 50.

While described above with reference to the exemplary method 50 of FIG. 4 and the automated assessment system 10 of FIG. 1, those of ordinary skill in the art will appreciate that components or subsystems of the system 10 may be used within the scope of the disclosure. For instance, the ECU 25 may be used with the image capture device 18, embodied as a high-speed camera, when diagnosing a zonular insufficiency condition. In an exemplary embodiment, the ECU 25 includes the above-noted processor(s) (P), the transceiver (Tx) in communication with the image capture device 18 and the visual target 22 of FIG. 1, and the memory (M) on which is recorded instructions for implementing the present method 50.

Execution of such instructions causes the processor(s) (P) to receive images of the eye 11, potentially inclusive of the P1 reflex and the P4 reflex, from the image capture device 18 when the electromagnetic energy (arrow LL) is directed onto the pupil 16 of the eye 11, as shown in FIGS. 1 and 2, and to transmit the optional dynamic gaze-guiding cue (arrow $CC_{22}$) to the visual target 22 to thereby move the visual target 22 or a display thereon sufficiently for inducing predetermined eye saccades, which may occur concurrently with the characteristic Purkinje reflexes in light-based embodiments. Execution of the instructions also causes the processor(s) (P) to compute one or more motion curves of the detected lens motion, extract time-normalized lens oscillation traces based on the curve(s), and model-fit the lens oscillation traces using one of the lumped mass models shown in FIGS. 5A-C to thereby diagnose the zonular condition.

The automated assessment system 10 of FIG. 1 and the accompanying method 50 described with reference to FIGS. 2-5C thus enable non-invasive diagnostics or assessment of lens/capsule conditions, as well as of residual accommodative potential/ciliary muscle activity and other possible beneficial ocular applications. The present teachings enable a practitioner to accurately infer the structural status of supporting structure within the eye 11, e.g., of the hidden zonules of the eye 11, via the metrics generated through the above-described motion tracking, analysis, and physical modeling set forth above. Thus, the present teachings may help improve pre-operative assessment. Likewise, the present teachings may be extended to post-operative situations, such as by assessing pseudo-phakic eyes to diagnose visual impairments linked to potential zonular problems of the types described hereinabove. These and other benefits will be readily appreciated by those of ordinary skill in the art in view of the present disclosure.

The detailed description and the drawings or FIGS. are supportive and descriptive of the disclosure, but the scope of the disclosure is defined solely by the claims. While some of the best modes and other embodiments for carrying out the claimed disclosure have been described in detail, various alternative designs and embodiments exist for practicing the disclosure defined in the appended claims.

Furthermore, the embodiments shown in the drawings or the characteristics of various embodiments mentioned in the present description are not necessarily to be understood as embodiments independent of each other. Rather, it is possible that each of the characteristics described in one of the examples of an embodiment can be combined with one or a plurality of other desired characteristics from other embodiments, resulting in other embodiments not described in words or by reference to the drawings. Accordingly, such other embodiments fall within the framework of the scope of the appended claims.

What is claimed is:

1. A method for assessing a lens capsule stability condition within an eye of a human patient, the method comprising:
   directing electromagnetic energy in a predetermined spectrum onto a pupil of the eye, via an energy source, concurrently subsequent to a movement of the eye causing eye saccades to occur therein;
   acquiring images of the eye indicative of the eye saccades using an image capture device;
   computing, via an electronic control unit (ECU) using the images, a motion curve describing motion of the lens capsule;
   extracting time-normalized lens capsule oscillation traces based on the motion curve via the ECU; and
   model-fitting the time-normalized lens capsule oscillation traces via the ECU to thereby assess the lens capsule instability condition.

2. The method of claim 1, wherein computing the motion curve includes computing a position curve, an instantaneous velocity curve, and/or an acceleration curve.

3. The method of claim 2, wherein the electromagnetic energy is light energy, the energy source is a light source, and the image capture device is a camera, and wherein acquiring images of the eye includes acquiring images of characteristic Purkinje reflexes within the eye.

4. The method of claim 3, wherein the characteristic Purkinje reflexes include a P1 reflex having P1 coordinates and a P4 reflex having P4 coordinates, the method further comprising subtracting the P1 coordinates from the P4 coordinates via the ECU to thereby correct for rotation of the eye.

5. The method of claim 3, wherein the characteristic Purkinje reflexes include a P1 reflex, and wherein computing the motion curve includes computing a motion curve of the P1 reflex.

6. The method of claim 1, further comprising transmitting a dynamic gaze-guiding cue to a visual target arranged along a line-of-sight of the eye to thereby induce the eye saccades.

7. The method of claim 1, wherein the image capture device is a high-speed camera, directing electromagnetic energy in the predetermined spectrum onto the pupil of the eye, via the energy source, includes directing a beam of infrared (IR) light onto the pupil, and acquiring images of the eye indicative of the eye saccades includes using a hot-mirror to direct reflected IR light from the eye toward the high-speed camera.

8. The method of claim 1, wherein directing electromagnetic energy in the predetermined spectrum onto the pupil of the eye includes using ultrasonic energy to directly image the lens capsule, and wherein acquiring images of the eye indicative of the eye saccades includes collecting ultrasonic images of the lens capsule.

9. The method of claim 1, wherein model-fitting the lens oscillation traces includes using a lumped mass model of a saccadic actuation force of the eye.

10. The method of claim 1, further comprising:
presenting different accommodative demands to the human patient via an optical lens while acquiring the images; and
using a non-linear lumped mass model to perform the model-fitting of the lens oscillation traces;
wherein diagnosing the latent lens capsule instability condition includes detecting ciliary muscle activity of the eye.

11. An automated system for assessing a lens capsule instability condition in an eye of a human patient, the system comprising:
an energy source configured to direct electromagnetic energy in a predetermined spectrum onto or into the eye concurrently with induced eye saccades;
an image capture device configured to acquire images of the eye indicative of the eye saccades; and
an electronic control unit (ECU) in communication with the energy source and the image capture device, wherein the ECU is configured to:
calculate a motion curve of the lens capsule using the images, wherein the motion curve is descriptive of motion of the lens capsule;
extract time-normalized lens oscillation traces based on the motion curve; and
model-fit the time-normalized lens oscillation traces to thereby assess the lens capsule instability condition.

12. The automated system of claim 11, wherein the electromagnetic energy is light energy, the energy source is a light source, and the image capture device is a high-speed camera, and wherein the images are of characteristic Purkinje reflexes within the eye.

13. The automated system of claim 12, wherein the characteristic Purkinje reflexes include a P1 reflex having P1 coordinates and a P4 reflex having P4 coordinates, wherein the ECU is configured to subtract the P1 coordinates from the P4 coordinates via the ECU to thereby correct for rotation of the eye.

14. The automated system of claim 12, wherein the characteristic Purkinje reflexes include a P1 reflex, and wherein the ECU is configured to compute the motion curve of one of the characteristic Purkinje reflexes by computing an instantaneous velocity curve, an instantaneous acceleration curve, and/or an instantaneous position curve of the P1 reflex.

15. The automated system of claim 11, further comprising a visual target, wherein the ECU is configured to transmit a dynamic gaze-guiding cue to the visual target to induce the eye saccades.

16. The automated system of claim 11, wherein the image capture device is a high-speed camera and the electromagnetic energy is a beam of infrared (IR) light, the automated system further comprising a hot-mirror configured to direct reflected IR light from the eye toward the high-speed camera.

17. The automated system of claim 11, wherein the energy source and/or the image capture device includes an ultrasonic transducer configured to directly image the lens capsule via ultrasonic energy, and wherein the ECU is configured to acquire images of the eye indicative of the eye saccades by collecting ultrasonic images of the lens capsule.

18. The automated system of claim 11, wherein the ECU is configured to perform the model-fitting of the lens oscillation traces using a lumped mass model of a saccadic actuation force of the eye.

19. An electronic control unit (ECU) for use with a high-speed video camera when diagnosing a lens capsule instability condition in an eye of a human patient, the ECU comprising:
a processor;
a transceiver in communication with the high-speed video camera; and
memory on which is recorded instructions, the execution of which by the processor causes the processor to:
receive images of the eye from the high-speed camera when an infrared (IR) light is directed onto a pupil of the eye, the images including a P1 characteristic Purkinje reflex;
transmit a dynamic gaze-guiding cue to the visual target to thereby move the visual target sufficiently for inducing predetermined eye saccades concurrently with the characteristic Purkinje reflexes;
compute an instantaneous velocity curve, acceleration curve, and/or position curve of the P1 characteristic Purkinje reflex describing motion of the lens capsule;
extract time-normalized lens oscillation traces based on the instantaneous velocity curve, acceleration curve, and/or position curve; and
model-fit the lens oscillation traces using a lumped mass model to thereby diagnose the zonular condition.

20. The ECU of claim 19, wherein the transceiver is coupled to an adjustable optical lens positioned along a line-of-sight between the human patient and the visual target, and wherein execution of the instructions causes the processor to acquire the images of the characteristic Purkinje reflexes while a different accommodative demand is presented to the human patient via the adjustable optical lens.

* * * * *